United States Patent [19]
Berger

[11] 4,081,685
[45] Mar. 28, 1978

[54] ARRANGEMENT FOR THE PREPARATION OF A BODY CROSS-SECTION IMAGE

[75] Inventor: Roland Berger, Bubenreuth, Germany

[73] Assignee: Siemens Aktiengesellschaft, Berlin and Munich, Germany

[21] Appl. No.: 737,261

[22] Filed: Nov. 1, 1976

[30] Foreign Application Priority Data

Nov. 12, 1975 Germany .............................. 2550868

[51] Int. Cl.² ............................................. H05G 1/30
[52] U.S. Cl. .......................... 250/416 TV; 250/445 T
[58] Field of Search ............................ 250/416, 445 T

[56] References Cited

U.S. PATENT DOCUMENTS 3,946,234  3/1976  Hounsfield ........................ 250/445 T

*Primary Examiner*—Davis L. Willis

*Attorney, Agent, or Firm*—Kenyon & Kenyon, Reilly, Carr & Chapin

[57] ABSTRACT

An arrangement for the preparation of a body cross-section image in which the picture elements of the body cross-section image are derived from the absorption of ionizing rays which penetrate the corresponding body elements in the body cross-sectional plane sequentially in different directions with the output signals of a multiplicity of detectors coupled as the input signal to electronic circuitry, an electronic switch is associated with each of the individual detectors and the control electrodes of all switches connected to a respective output shift register. A common load resistor is associated with all detectors, the voltage of the load resistor being provided as the input signal to the electronic circuitry so as to require only a single, common output line for the output signals of all detectors which must be brought out of the image convertor.

6 Claims, 4 Drawing Figures

ARRANGEMENT FOR THE PREPARATION OF A BODY CROSS-SECTION IMAGE

BACKGROUND OF THE INVENTION

This invention relates to apparatus for the preparation of a body cross-sectional image utilizing ionizing rays in general and more particularly to an improved apparatus in which the output signals of a multiplicity of detectors which are coupled to electronic circuitry can be brought out of an image convertor or a cyrostat on a single common output line.

Apparatus is known for the preparation of a body cross-section image having picture elements which are derived from the absorption of ionizing rays which penetrate the corresponding body element in the body cross-section plane sequentially in different directions. In such apparatus a multiplicity of detectors arranged side by side in the body cross-section plane are utilized to detect the amount of absorption of the rays. The electrical output signals of the detectors are provided an inputs to electronic circuitry.

Arrangements of this general nature for the preparation of a body cross-section image in which the body is scanned by parallel displacement of the radiation source and the radiation receiver and the body cross-section plane are known as scanners. In such devices an X ray or gamma ray source generates a bundle of parallel rays which penetrate the body to be examined in the cross-section plane and a certain portion of which rays are absorbed by the body. An image detector or carrier is disposed behind the body to be examined with the radiation, which after a portion of it has been absorbed, strikes the image carrier. By means of a stepwise parallel displacement of the radiation source and image carrier, the body elements are scanned sequentially in a cross-sectional plane. Subsequently, the radiation source and the image carrier are tilted through a predetermined angle with respect to an axis extending perpendicular to the cross-section plane and the body part cross-section plane is again projected on the image carrier by parallel displacement. The individual picture elements are thus penetrated by the radiation in a different direction. If this process is repeated a number of times, each body element in the cross-section plane is imaged as many times as the system is tilted about the axis. The conversion of the different individual measurements of the body elements and their correlation to the corresponding picture element of the body cross-section image to be prepared are obtained by means of electronic circuitry in a computer which utilizes, for example, 28,800 equations with 6,400 variables to carry out the image processing.

In one particular embodiment of such a device, the fan shaped radiation of a radiation source is subdivided into individual ray bundles lying in the cross-sectional plane by means of separate collimators. This is done to shorten the time required to generate the data necessary to produce a body cross-section impage. Behind the body a plurality of photodetectors is provided having associated therewith a common reference scintillator. The output signals of the photomultipliers are further processed in electronic circuitry and then control a printer which furnishes the body cross-sectional image. Such as disclosed in German Offenleichenshaft 1,941,433. In the disclosed arrangement for the preparation of a body cross-section image using a fan shapped ray bundle and a plurality of detectors in the radiation receiver, each individual detector furnishes a separate output signal which is fed to the electronic circuitry for further processing.

Thus, for each detector a separate output line from the radiation receiver is therefore necessary. This requires considerable expense, particularly if the radiation receiver is operated in a vacuum or if semiconductor detectors which must be kept in a low temperature in a special cooling device are utilized, i.e., semiconductor detectors disposed in a cryostat.

In view of these problems with bringing out separate lines it is the object of the present invention to provide a simplified information readout for a multiple detector arrangement of this nature.

SUMMARY OF THE INVENTION

In accordance with the present invention, this object is achieved by providing an electronic switch for each individual detector, the switch having a control electrode with the control electrodes of the switches coupled to respective outputs of a shift register. A common load resistor, whose voltage drop is provided as the input signal for the electronic circuitry which is supplied with data, is associated with all detectors. By the use of this arrangement the output signals of the individual detectors are read sequentially at the common load resistor and fed to the electronic circuitry on a single output line.

The detectors are sequentially scanned at the clock rate of the shift register. In operation, the detectors are radiated, a sweep cycle of the shift register carried out and then the detectors again radiated. Thus, the radiation receiver requires, in addition to the supply lines for the shift register and detectors, only a single common output line from a multiplicity of detectors. For example, 256 or more detectors can be coupled to a single common output line.

DETAILED DESCRIPTION OF THE INVENTION

Figure 1:
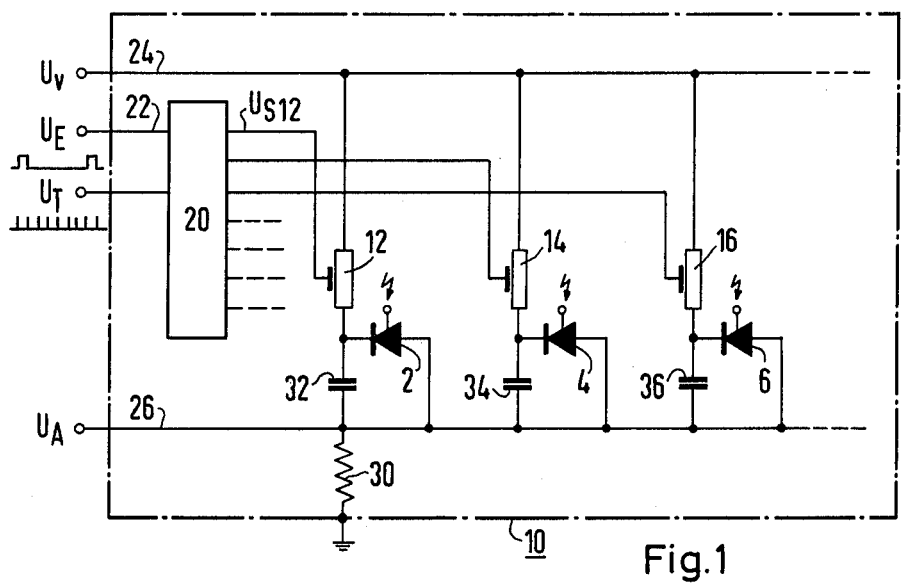
FIG. 1 is a schematic diagram illustrating the arrangement according to the present invention.

As illustrated by FIG. 1, a plurality of detectors, of which only three detectors 2, 4 and 6 are shown on the figure for sake of simplicity, are arranged in a radiation receiver 10 used for the preparation of a body cross-section image. As noted above, a large plurality up to 256 or more detectors such as detectors 2, 4 and 6 may be used. As noted above, in some cases such a receiver must be in a special environment such as in a vacuum or in a cooled environment, i.e., in a cryostat. The semiconductor detectors 2, 4 and 6 are the type with a semiconductor body sensitive to an ionizing radiation. Each of these detectors 2, 4 and 6 receive a portion of the fan shaped radiation of the radiation source which is not shown in the figure. The incident radiation on these semiconductor detectors is indicated by the lightning arrows thereabove. Each detector is preceeded by an electronic switch, preferably a field effect transistor and more specifically an mos (metal oxide semiconductor) transistor. Transistor 12 is associated with the detector 2, transistor 14 with detector 4 and transistor 16 with detector 16. The control electrodes of these switches or transistors are connected to respective outputs of a shift register 20. Shift register 20 includes an input voltage $U_E$ on line 22 and has a clock pulse input designated $U_T$. In conventional fashion, the clock pulses on the terminal $U_T$ will cause the data at the input on line 22 to be shifted through the successive stages of the shift register which will in turn provide outputs on the individual lines. The sources of each of the transistors 12, 14 and 16 are connected to a supply voltage line 24 having a voltage $U_V$ thereon which may be, for example 50 volts. The drains of the individual transistor switches 12, 14 and 16 are connected to the detectors 2, 4 and 6. The other side of the detectors 2, 4 and 6 are connected to a common bus 26 having an output which is designated $U_A$ and which is coupled to ground through a resistor 30. Each detector also has thereacross a capacitor, the capacitor 32 being associated with detector 2, capacitor 34 with detector 4 and capacitor 36 with detector 6. This is an optional measure. The necessity of using such capacitor will depend on the particular detectors used.

Figure 2:
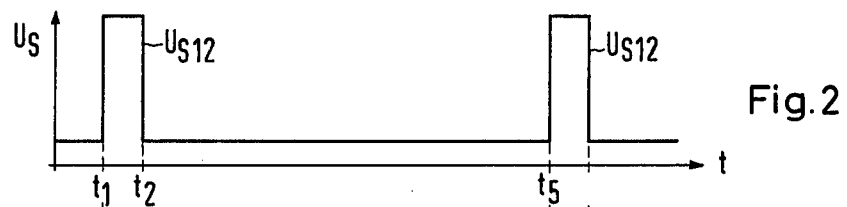
FIGS. 2, 3 and 4 are waveform diagrams helpful in understanding the operation of the apparatus of FIG. 1.
Figure 3:
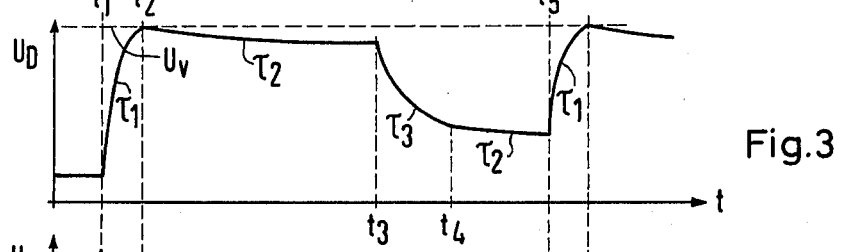
Figure 4:
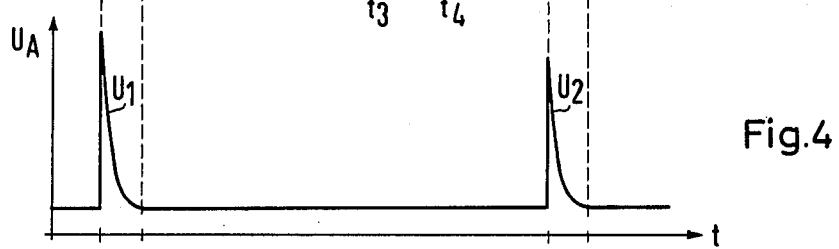

FIG. 2 is a plot of the control voltage $U_S$ for the individual detectors verses time T. In particular, $U_{S12}$ from the first output of shift register 20 and which is coupled to the control electrode of the switch 12 is shown. At time $t_1$ a clock pulse appears at the input to the shift register 20. This results in the first output of the shift register going positive as shown. This pulse opens the switch 12 and the voltage $U_D$, illustrated on FIG. 3, at the detector 2 rises with a time constant $\tau_1$ which is determined by the internal capacity of the detector and, if one is supplied, by supplemental capacitor 32 as well as by the load resistor 30 which typically would be about 100 ohms. FIG. 3 illustrates this rising waveform as a function of time $t$. The voltage of the detector 2 rises exponentially with the time constant $\tau_1$ until it has at least approximately reached the value of the supply voltage $U_V$ at the time $t_2$. The output pulse across the resistor 30 and which is provided at the output terminal $U_A$ is shown on FIG. 4. The charging current for the detector results in a corresponding voltage drop $U_1$ at the load resistor 30 which in turn results in a corresponding output on the line 26.

At time $t_2$, the control pulse $U_{S12}$ is terminated and the switch 12 is closed. The duration of the control pulse $U_{S12}$ must be longer than the time constant $\tau_1$. As soon as the switch 12 is closed, the discharge of the detector through its internal resistance begins with a correspondingly large time constant $\tau_2$. If a radiation pulse arrives at the detector 2 at the time $t_3$, then the electron-hole pairs generated in the bulk of the detector by the incident radiation reduce its internal resistance by several orders of magnitude and discharge takes place with a correspondingly increased time constant $\tau_3$. At time $t_4$ it is assumed that the radiation pulse is over and the discharge of the detector 2 continues with the time constant $\tau_2$. At the time $t_5$, a further control pulse $U_{S12}$ opens the switch 12 and the detector voltage $U_B$ rises with the time constant $\tau_1$ to the value of the supply voltage $U_V$ again. Since a residual charge was still present in the detector 2 an output pulse on line 26 $U_2$ of smaller magnitude is now obtained. If, with the next incident radiation pulse an absorbing medium, the cross-section image of which is to be displayed, is placed between the radiation source and the radiation receiver, the output pulse produced will again have a small amplitude. The difference of amplitudes of the output pulses, i.e., the difference between the pulse $U_2$ and other pulses, not illustrated on the figure, is thus a measure of the absorption in the body cross-section plane.

All switches 12, 14 and 16 respectively which are associated with the detectors 2, 4 and 6 are sequentially switches at the frequency of the shift register within the time period between $t_1$ and $t_5$. In other words between the pulses shown on FIG. 2 pulses will have been provided to each of the detectors used. As a result, the clock frequency of the shift register 20 and the frequency of the radiation pulses are therefore chosen so that the scanning of the detectors is completed at the time when they are again irradiated. With 256 detectors in the receiver 10, the spacing in time of the initial pulse $U_E$ which is loaded into the shift register may be, for example, 60 milliseconds. After that time, a new sweep cycle of the shift register 20 and a new scanning cycle therefor begin.

The output pulses $U_A$ are processed sequentially in electronic circuitry and compared with the output pulses $U_2$ obtained when no absorbing intermediate medium was in place. In other words the pulses $U_2$ serve as callibrating pulses.

The connection of the additional capacitors 32, 34 and 36 in parallel with the detectors as illustrated on FIG. 1 are advantageous where the capacity of the detectors used is relatively small. With the supplementary capacitors, the discharge time constant of the parallel circuit consisting of the detector and the supplemental capacitor is correspondingly increased and only a correspondingly small discharge is obtained in a time period from $t_2$ to $t_5$.

A spacially resolving detector arrangement having a multiplicity of individual detector with a radiation sensitive semiconductor body may be used as the radiation receiver. The features of the present invention are particularly applicable to a receiver having semiconductor detectors, the bodies of which must be kept at cryogenic temperatures in a cryostat. In such a case the housing of the radiation receiver 10 can be further provided with detectors for electron rays and can operate in the manner of an X-ray image converter. In such operation the rays penetrating the body to be examined in the cross-section plane the released electrons in a photocathode which are accelerated in the vacuum secton and fed to the detectors. In such devices, the supply lines and common output line must be brought out of the housing of the image convertor. Naturally, since there is a substantial reduction of the number of wires which must be brought out of such an environment, the present invention is particularly beneficial in such a case.

What is claimed is:

1. In an arrangement for the preparation of a body cross-section image in which picture elements are derived from the absorption of ionizing rays which penetrate the corresponding body element in the body cross-section plane in different directions, which arrangement includes a multiplicity of detectors arranged side by side in the body cross-sectional plane with the electrical signals from the detectors provided as inputs to electronic circuitry which carries out image processing therefrom, the improvement comprising:
   a. an electronic switch associated with each detector coupling one side thereof to a positive voltage, each of said switches having a control electrode;
   b. a shift register having its respective outputs coupled to the control electrodes of said switches;

c. a common load resistor coupling the other sides of all said detectors to a reference potential; and d. means for coupling the voltage across said resistor as the input for the electronic circuitry.

2. Apparatus according to claim 1 and further including a supplemental capacitor coupled in parallel across each of said detectors.

3. Apparatus according to claim 1 wherein said electronic switches comprise MOS field effect transistor switches.

4. Apparatus according to claim 3 wherein said reference potential is ground.

5. Apparatus according to claim 1 wherein said detectors, switches and shift register are contained within an enclosure which is cooled to a low temperature.

6. Apparatus according to claim 1 wherein at least 256 detectors are employed each coupled in common to said resistor.

* * * * *